United States Patent [19]

Nysted et al.

[11] Patent Number: 4,670,569

[45] Date of Patent: Jun. 2, 1987

[54] 5-FLUORO-PGI$_2$ COMPOUNDS

[75] Inventors: Leonard N. Nysted, Highland Park, Ill.; Raphael Pappo, Redwood City, Calif.

[73] Assignee: G. D. Searle & Co., Skokie, Ill.

[21] Appl. No.: 709,879

[22] Filed: Mar. 8, 1985

Related U.S. Application Data

[63] Continuation of Ser. No. 513,469, Jul. 13, 1983, Pat. No. 4,540,801, which is a continuation-in-part of Ser. No. 250,530, Apr. 2, 1981, abandoned.

[51] Int. Cl.$^4$ .......................................... C07D 307/935
[52] U.S. Cl. ..................................... 549/465; 540/544; 540/596; 544/153; 544/335; 544/376; 546/196; 548/525
[58] Field of Search ................ 549/465; 540/544, 596; 544/153, 335, 376; 546/196; 548/525

[56] References Cited

U.S. PATENT DOCUMENTS 4,324,730  4/1982  Fried ................................... 549/465

FOREIGN PATENT DOCUMENTS 0062303  11/1985  European Pat. Off. .
56-2979   1/1981  Japan .

OTHER PUBLICATIONS

Bindra et al., Prostaglandin Synthesis, Academic Press, pp. 71-75 (1977).
Nakai et al., Chem. Letters, pp. 1499-1502 (1979).
Bannai et al., Yuki Gosei Kagaku Kyokashi, 42(9), pp. 794-808 (1984).

Primary Examiner—John M. Ford
Assistant Examiner—Bernard I. Dentz
Attorney, Agent, or Firm—Paul D. Matukaitis; J. Timothy Keane

[57] ABSTRACT

The present invention relates to 5-fluoro-PGI$_2$ derivatives of Formula I. These compounds are useful for the treatment of platelet dysfunction. Also disclosed is the process for preparing them and the appropriate intermediates.

3 Claims, No Drawings

5-FLUORO-PGI₂ COMPOUNDS

BACKGROUND OF THE INVENTION

This application is a continuation of application Ser. No. 513,469 filed July 13, 1983, now U.S. Pat. No. 4,540,801, which latter application was a continuation-in-part of application Ser. No. 250,530 filed Apr. 2, 1981 now abandoned.

This invention relates to prostaglandin derivatives and to a process for preparing them. More particularly the invention relates to novel prostacyclin derivatives, in particular $PGI_2$ derivatives. More particularly, this invention relates to $PGI_2$ derivatives of formula I Chart A.

The prostaglandins and analogs are well-known organic compounds derived from prostanoic acid which has the structure and atom numbering shown in FIG. II Chart A.

As drawn hereinafter the formulas represent a particular optically active isomer having the same absolute configuration as $PGI_2$.

In the formulas, broken line attachments to the cyclopentane ring or side chain indicate substituents in alpha configuration, i.e. below the plane of the cyclopentyl ring or side chain. Heavy solid line attachments indicate substitutents in beta configuration, i.e. above the plane.

For background on prostaglandins, see for example Bergstrom et al., Pharmacol. Rev. 20, 1 (1968). For related compounds see Pace-Asciak et al., Biochem. 10 3657 (1971). Related compounds are described in publication on 6-keto-prostaglandin $F_{1\alpha}$ by Pace-Asciak, J. Am. Chem. Soc. 2348 (1976) and a publication on "PGX" (6,9α-oxido-9α,15-dihydroxyprosta(Z)5,(E)13-dienoic acid) by E. J. Corey et al., J. Am. Chem. Soc. 99, 20006 (1977).

The compounds of this invention may be regarded as analogs of prostacyclin and prostacyclin type compounds.

Prostacyclin, an organic compound related to prostaglandins, is (5Z)-9-deoxy-6,9α-epoxy-Δ⁵-PGF₁ and is represented by formula III of Chart A. For its synthesis and structure see for example R. A. Johnson et al., J. Am. Chem. Soc., 99, 4182 (1977) and Prostaglandins 12, 915 (1976), and E. J. Corey et al., cited above. For some of its biological properties uses see the references cited in the Johnson references. Prostacyclin is referred to as "$PGI_2$", see Anonymous, Prostaglandins, 13, 375 (1977).

Prostaglandins and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestinal effects from systemic administration of prostaglandin synthetase inhibitors.

Because of these biological responses, prostaglandins and prostacyclin-type compounds are useful to study, prevent, control, or alleviate a wide variety of diseases and undersirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent postoperative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intrevenous route of administraton is preferred. Doses in the range about 0.01 to about 10 mg per kg of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preseved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the perfused body portion, attached or detached, to the recipient, or to two or all of those at a whole blood. These compounds are also useful in preparing platelet-rich concentrates from blood for use in treating thrombocytopenia or in chemotherapy.

Prostglandins E, F and related compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulator, for example, to relieve the symptoms of paralytic ileus, or to control or prevent atonic uterine bleeding after abortion or delivery, to aid in expulsion of the placenta, and during the puerperium. For the later purpose, the compound is administered by intravenous infusion immediately after abortion or delivery at a dose in the range about 0.01 to about 50 mcg per kg of body weight per minute until the desired effect is obtained. Subsequent doses are given by intravenous, subcutaneous, or intramuscular injection or infusion during puerperium in the range 0.01 to 2 mg per kg of body weight per day, the exact dose depending on the age, weight, and condition of the patient or animal.

Prostaglandins and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramusclarly in an infusion dose range about 0.1 mcg per kg of body weight per minute, or in a total daily dose by injection of infusion in the range about 0.01 to about 10 mg per kg of body weight per day, the exact dose depending on the age, weight, and condition of the patient or animal, and on the frequency and route of administration.

Prostaglandins and prostacyclin-type compounds are also useful in reducing the undesirable gastrointestinal effects resulting from systemic administration of anti-inflammatory prostaglandin synthetase inhibitors, and are used for that purpose by concomitant administration of prostaglandins or prostacyclin-type compound and anti-inflammatory prostaglandin synthetase inhibitor. See Partridge et al., U.S. Pat. No. 3,781,429, for a disclosure that the ulcerogenic effect induced by certain non-steroidal and steroidal anti-inflammatory agents in rats is inhibited by concomitant oral administration of certain prostaglandins of the E and A series, including $PGE_1$, $PGE_2$, $PGE_3$, 13, 14-dihydro-$PGE_1$, and the corresponding 11-deoxy-PGE and PGA compounds. Prostaglandins and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory synthetase inhibitor, for example and indomethacin, aspirin, or phenylbutazone is administered in any of the ways known in the art to alleviate an inflammatory condition, for example, in any dosage regimen and by any of the known routes of systemic administration.

The prostaglandins or prostacyclin-type compound is administered along with the anti-inflammatory prostaglandin synthetase inhibitor either by the same route of administration or by a different route. For example, if the anti-inflammatory substance is being administered orally, the prostaglandins or prostacyclin-type compound is also administered orally, or alternatively, as administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin or prostacyclin-type compound is also administered rectally. Further, the prostaglandin or prostacyclin derivative can be conveniently administered orally or, in the case of women, vaginally. It is especially convenient when the administration route is to be the same for both anti-inflammatory substance and prostaglandin or prostacyclin-type compound to combine both into a single dosage form.

The dosage regimen for the prostaglandin or prostacyclin-type compound in accord with this treatment will depend upon a variety of factors, including the type, age, weight, sex and medical condition of the mammal, the nature and dosage regimen of anti-inflammatory synthetase inhibitor being administered to the mammal, the sensitivity of the particular prostaglandin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of anti-inflammatory substance is causing undersirable gastrointestinal effects in the human or animal subject and to prescribe an effective amount of the prostaglandin or prostacyclin-type compound to reduce and then substantially to eliminate those undesirable effects.

Prostaglandin or prostacyclin-type compounds are also useful in the treatment of asthma. For example, these compounds are useful as bronchodilators or as inhibitors of mediators, such as SRS-A, and histamine which are released from cells activated by an antigen antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of supporitories; parenterally, subcutaneously, or intramuscalarly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use the prostaglandin or prostacyclin-type compound can be combined advantageously with other asthmatic agents, such as sympathomimetics (isoproterenol, phenylephrine, ephedrine, etc.); xanthine derivatives (theophylline and aminophylline); and corticosteroids (ACTH and prednisolone).

Prostaglandin or prostacyclin-type compounds are effectively administered to human asthma patients by oral inhalation or aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stablize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the above ingredient suspended in an inert propellant (such as a mixture of dichlorodifluoromethane and dichlorotetrafluoroethane) together with a co-solvent, such as ethanol, flavoring materials and stabilizers. Instead of a co-solvent there can be used a dispensing agent such as oleyl alcohol. Suitable means to employ the aerosol inhalation therapy technique are described fully in U.S. Pat. No. 2,868,691 for example.

Prostaglandins or prostacyclin-type compounds are useful in mammals, including man, as nasal decongestants and are used for this purpose in a dose range of about 10 mcg to about 10 mg per ml of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart, the microvasculature serving the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, nonobstructive mesenteric ischemia, arteritis lymphangitis and the like. These examples are included to be illustrative and should not be construed as limiting the term peripheral vascular disease. For these conditions the prostacyclin compounds are administered orally or parenterally via injection or infusion directly into a vein or artery.

The dosages of such compounds are in the range of 0.01-10 mcg administered by infusions at an hourly rate or by injection on a daily basis, i.e. 1-4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No. 74/0149 referenced as Derwent Farmdoc No. 58,400V. See Elliott et al., Lancet Jan. 18, 1975, pp. 140-142. Prostaglandins or prostacyclin-type compounds are useful in place of oxytocin to induce labor in pregnant female animals with intrauterine death of the fetus from about 20 weeks to term. For this purpose, the compound is infused intravenously at a dose of 0.01 to 50 mcg per kg of body weight per minute until or near the termination of the second stage of labor i.e., explusion of the fetus. These compounds are especially useful when the female is one or more weeks post-mature and natural labor has not started, or 12 to 60 hours after the membranes have ruptured and natural labor has not yet started. An alternative route of administration is oral.

Prostaglandins or prostacyclin type compounds are further useful for controlling the reproductive cycle in menstruating female mammals, including humans. By the term menstruating female mammals is meant animals which are mature enough to menstruate, but not so old that regular menstruation has ceased. For that purpose the prostaglandin compound is administered systemically at a dose level in the range 0.01 mg to about 20 mg per kg of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostaglandin or prostacyclin-type compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandin compounds is also useful in operative gynecology such as D and C (Cervical Dilation and Uterine Curettage) where mechanical dilation may cause performation of the uterus, cervical tears, or infections. It is also useful for diagnostic procedures where dilation is necessary for tissue examination. For these purposes, the prostacyclin compound is administered locally or systemically.

The prostaglandin compound, for example, is administered orally or vaginally at doses of about 5 to 50 mg per treatment of an adult female human, with from one to five treatments per 24 hour period. Alternatively the compound is administered intramuscularly or subcutaneously at doses of about one to 25 mg per treatment. The exact dosages for these purposes depend on the age, weight, and condition of te patient or animal.

Prostaglandins and prostacyclin-type compounds are further useful in domestic animals as in abortifacients (especially for feedlot heifer), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin compound is injected or applied in a feed at doses of 0.1-100 mg per animal and may be combined with other agents such as steroids. For example, mares are given the prostaglandin compound 5 to 8 days after ovulation and return to estrus. Cattle are treated at regular intervals over a 3 week period to advantageously bring all into estrus at the same time.

Prostaglandin or prostacyclin-type compounds increase the flow of blood in the mammalian kidney, thereby increasing volume and electrolyte content of the urine. For that reason, these compounds are useful in managing cases of renal dysfunction, especially those involving blockage of a renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 mcg per kg of body weight per minute until the desire effect is obtained. Subsequent doses are given by intravenous, intramuscular, or subcutaneous injection or infusion in the range 0.05 to 2 mg kg of body weight per day.

Prostaglandin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and aquamous cell carcinomas of the skin, lamellar ichtyhosis, epidermolytic hyperkeratosia, premalignant sun-induced keratosis, nonmalignant keratosis, acne, and seborrheic dermatitis in humans and atopic dermatitis and mange in domesticated animals. These compounds alleviate the symptoms of these proliferative skin disease: psoriasis, for example, being alleviated when a scale-free psoriasis lesion is noticeably decreased in thickness or noticeably but incompletely cleared or completely cleared.

For those purposes, such compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostaglandin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent in incorporated herein by reference.

Antiplatelet substances such as $PGI_2$ are known and have been used to afford relief from the aggregate condition.

$PGI_2$ is a notably unstable substance. Although effective, $PGI_2$ often affords unwanted hypotensive effects. Also the antiplatelet aggregation effect is short lived and the hazardous condition of sticky platelet returns quickly.

The compounds of the instant invention are novel in that, compared to natural occurring $PGI_2$, they are surprisingly more stable and are active against platelet aggregation over a longer period of time. In addition, the compounds of the present invention show a surprising and unexpected decrease in hypotensive effects.

The instability of $PGI_2$ is largely due to the chemical readiness to decompose via the opening of an enolic cyclic ether under neutral or acidic conditions. The hydrolysed compound is either inactive or shows a marked decrease in activity. The compounds of the instant invention are more stable because the placement of a fluorine atom at the 5 position. This reduces a partial charge build up on the oxygen atom which is a prerequisite to protonization and subsequent hydrolysis.

PRIOR ART

PGI derivatives and prostacyclin derivatives are well known in the art as described above. U.S. Pat. Nos. 4,123,444 and 4,124,599 described PG derivatives namely prostacyclins. These patents describe 5 and 6 keto substituents as well as 9-deoxy-9-deoxo-9-hydroxymethyl substituents. The patents are described as having general prostaglandin activity. U.S. Pat. No. 4,145,535 relates to certain trans-4,5-didehydro-PGI compounds which are also stated to exhibit general prostacyclin like properties. U.S. Pat. No. 4,233,121 describes certain 5-halo-6,9-oxido prostaglandin derivatives which have anticoagulant activity.

SUMMARY OF THE INVENTION

The present invention particularly provides:

1. A compound of formula I wherein $R_1$ is:
   (a) $OR_2$;
   (b) $NR_3R_4$
   (c)

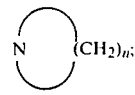

(d)

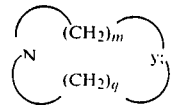

wherein $R_2$ is
(a) Na, K, or $\frac{1}{2}$ Ca;
(b) hydroxyalkyl of 1 to 6 C atoms;
(c) hydrogen;
(d) alkyl of 1 to 6 carbon atoms;
wherein $R_3$ is
(a) hydrogen; or
(b) alkyl of 1 to 6 carbon atoms, inclusive;
wherein $R_4$ is:
(a) hydrogen; or
(b) alkyl of 1 to 6 carbon atoms, inclusive;
wherein n is an integer from 4 to 5; wherein m and q are integers and taken together equal 4 to 5 wherein Y is:
(a) O
(b) NH
wherein X is:
(a)

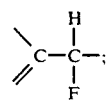

or
(b) $>C(R_5)-CHF-$
wherein $R_5$ is alkoxy from 1 to 6 carbon atoms and the individual isomers either alone or in combination; and the pharmacologically acceptable salts thereof.

The test proceudre (ex vivo cat) used to determine Platelet function is as follows:

Experimental animal—cats, body weight 2–4 kg, were anesthetized intraperitoneally with pentobarbital (35 mg/kg). Cats of both sexes are used.

Both the right jugular vien and the right carotid artery were exposed. The right jugular vein was cannulated with siliconized PE tubing. After cannulation of the vein, 2500 units/kg heparin was infused into the cannula. The right cartoid artery was cannulated (siliconized PE 160 tubing) and arterial blood was withdrawn by a Holter roller pump (Model No. RL175) at a speed of 3 ml/min. The blood was superfused over a rabbit Achilles tendon cleaned of extraneous tissue. This tendon was suspended by means of surgical silk (Ethicon 000) from a Narco Bio-Systems F-60 myograph. After passage over the tendon, the blood was collected into a siliconized plastic funnel feeding into an Abbott intravenous drip apparatus. The blood was then returned to the cat via the jugular cannula using a Sigmamotor roller pump (Model No. AL-2-E). All tubing was previously siliconized and allowed to dry overnight. The increase in weight of the tendon was measured and recorded on a Narco Bio-Systems Physiograph (Model No. DMP-4A).

Achilles tendons used in the experiment were removed from sacrificed rabbits. Adhering tissues were removed by scraping the tendon. Tendons were collected and stored in saline at 4° C. until use (usually within one week). Prior to use, the tendons were scraped, replaced in saline to allow rehydration, and then weighed on a Sartorius balance. Tendons were used for one experiment and discarded.

Drugs were dissolved in ethanol or saline and an aliquot of ethanol (less than 100 mcl) or saline added to 0.5 ml saline. Solutions were infused into the cat through a side port on the venous return system by means of a (Harvard apparatus) syringe infusion pump set to deliver 0.5–1.0 ml of solution per minute. Ideally, infusions were initiated 30–60 minutes after the start of blood superfusion over the tendon. At least 20–30 minutes lapsed between successive dose infusions.

Heparin treatment was renewed every 2–3 hours. Saline was used to maintain blood pressure to compensate for the blood volume of the reservoir and tubing. Saline was also superfused over the tendon for baseline measurements prior to blood superfusion.

During some tests, blood samples were removed (0.5 ml) after passing over the tendon for further analysis of 6-keto $PGF_1$ or $TXB_2$ levels by radioimmunoassay.

Changes in the mass of platelets adhering to the tendon were recorded as weight change of the tendon. Weight of the tendon and the accumulated platelets just prior to drug infusion of each dose was considered to be maximum platelet mass on the tendon or 100%. Changes in platelet adhesion were measured by changes in weight and percent change in the platelet mass was calculated from the mass accumulated just prior to each dose of drug infused.

$PGI_2$ was used at the end of negative experiments to confirm platelet responsiveness. See Gryglewski, et al, Pharm. Res. Comm. Vol. 10, No. 2, 185–189(1978).

The lack of hypotensive effect was determined by the following procedure:

Surgical Preparation

Male Charles River CD strain rats weighing approximately 200 to 300 grams were anesthetized with Pentobarbital Sodium (50 mg/kg i.p.). The trachea was cannulated with polyethylene tubing to assist respiration. The right carotid artery and jugular vein were cannulated with polyethylene tubing for measurement of pulsatile blood pressure and injection of test substances respectively. The animals were maintained at a body temperature of 35° C. by means of a thermostatically controlled heating unit. Blood pressure was measured by means of a Micron MP-15 pressure transducer. The maximum decrease in diastolic pressure in response to individual injections was used as a measure of hypotensive activity.

Compound Preparation and Dosing $PGI_2$ and novel compounds were solubilized in 0.04M glycine buffer solution. $PGI_2$ was used at a concentration of 1 mcg/ml and the novel compounds were used at a concentration of 50 mcg/ml. $PGI_2$ injections were followed by short-lived blood pressure decreases that rapidly returned to preinjection levels. Intravenous $PGI_2$ doses were administered in ascending order and ranged from 0.01 to 0.15 mg/rat, while the novel compounds were given over a range of 50 to 200 mcg/rat. Following each injection the maximum decrease of diastolic blood pressure was noted. The blood pressure was allowed to return to or near to baseline level before the next larger challenge was given. Only one set of challenges of each compound was administered per rat. The order of dosing with compounds was randomized and the total number of rats used was 10.

Calculations

The maximum decreases of diastolic pressure were expressed as % of pre-injection baseline diastolic blood pressure. The relative potency calculations for the novel compound against $PGI_2$ were carried out. In this bioassay $PGI_2$ was assumed to have a potency of 1.0 and the relative potency of the other compounds is expressed as a fraction of $PGI_2$.

By virtue of this platelet aggregation activity the compounds of formula I are useful in treating platelet dysfunction in humans and animals. A physician or veterinarian of ordinary skills could readily determine a subject who is exhibiting platelet dysfunction symptoms. Regardless of the route of administration selected, the compounds of the present invention are formulated into pharmaceutically acceptable dosage forms by conventional methods known to the pharmaceutical arts.

The compounds can be administered in such oral unit dosage forms such as tablets, capsules, pills, powders, or granules. They also may be administered rectally, vaginally in such forms as suppositories, creams, enemas or bougies; they may also be introduced in the form of eye drops, interperitoneally, subcutaneously, or intramuscularly, using forms known to the pharmaceutical art. In general, the preferred form of administration is orally.

An effective but non-toxic quantity of the compound is employed in treatment. The dosage regimen for preventing or treating platelet dysfunction by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the agent to prevent or arrest the progress of the condition. In so proceeding, the physician or veterinarian could employ relatively low dosages at first, subsequently increasing the dose until a maximum response is obtained.

The acidic compounds of this invention can also be administered as pharmacologically acceptable basic salts such as sodium, potassium and calcium.

The starting substance used for the synthesis of the novel compounds is $PGI_2$ methyl ester formula XI of Chart B. $PGI_2$ methyl ester reacts with perchloryl fluoride in a protic solvent such as methanol. The resulting 5-fluoro-6-methoxy-PGI methyl ester, formula XII of Chart B, is then optionally silylated with triethylsilyl chloride in dry pyridine or DMF and imidazole. The resulting 11,15 bis-triethylsilyloxy-5-fluoro-6-methoxy-PGI methyl ester formula XIII of Chart B, is then refluxed and pyrolytically demethoxylated in t-butylbenzene for 5 to 90 minutes to afford the $\Delta^5$ fluoro compound formula XIV of Chart B, or the $\Delta^{6,7}$-5-fluoro compound, formula XVI ($R_1 = OCH_3$) of Chart B. The resulting compounds may be then deprotected by treating with KF in DMF for 48 hours to remove the triethylsilyl groups to yield formula XV of Chart B or formula IV ($R_1 = OCH_3$) Chart A. The respective compounds are then saponified over a 24 to 48 hour period to yield formula XXI of Chart C or formula IV ($R_1 = OR_2$) of Chart A. The resulting compounds have been shown to have platelet disaggregation properties comparable to PGI$_2$ with only a small percent of the hypotensive activity.

The compounds of formula XXII of Chart C are prepared directly from PGI$_2$ methyl ester, formula XI, described above. This is accomplished via treatment of the methyl ester with the appropriate amine in an alcoholic solution. Compound XXII is then silylated as previously described to yield formula XXIII of Chart C. After pyrolytic demethoxylation as described above, the silyl groups are then removed via the process previously described to yield compounds of formula XXV of Chart C or formula IV (R$_1$, OR$_2$) of Chart A. The compounds of formula XXVI of Chart C are prepared from the PGI$_2$ methyl ester by the process used to make the compounds of formula XXI of Chart C using an appropriate hydroxide.

The compounds or intermediates of the invention may also be separated or partially separated into individual isomers or groups of isomers using chromatography or other means known in the art.

DESCRIPTION OF THE PREFERRED EMBODIMENTS

EXAMPLE 1

Preparation of 5-fluoro-6 methoxy-PGI methyl ester (formula XII of Chart B)

PGI$_2$ methyl ester (500 mg) was dissolved in 5 milliliters of methanol in which was suspended by stirring 500 mg of dry sodium carbonate. To the suspension was added dropwise 15 ml of a solution of ClO$_3$F in carbon tetrachloride. The ClO$_3$F solution was prepared by condensing 1 gm of ClO$_3$F in a small dry ice trap and then dwastilling the ClO$_3$F into 58 milliliters of cold (−10° C.) carbon tetrachloride.

The methanol-carbon tetrachloride solvent mixture was blown down under a stream of nitrogen gas and a residue was extracted with methylene chloride. The resulting solution after centrifuging and decanting, was reduced to an oil under nitrogen and vacuum. The weight of the residue oil was 400 mg of title compound.

EXAMPLE 2

Preparation of 11,15-bis-triethylsilyloxy-5-fluoro-6-methoxy-PGI methyl ester (formula XIII of Chart B)

The product of example 1 (290 mg) was dissolved in 0.5 ml of dry pyridine in a sealed vial equiped with a small magnetic stirrer. Triethylsilylchloride (0.5 ml) was added to the solution and the reaction stirred overnight. The solid that forms was separated by centrifigation and washed with solvent and several portions of petroleum ether. The washings are then added to the pyridine solution and the combined parts washed with equal volumes of water several times and then dried by centrifugation and pipette. The petroleum ether solution was reduced to an oil under nitrogen gas and dried under vacuum and redissolved in petroleum ether for low pressure column separation. Elution with a 5% ethyl acetate-petroleum ether solvent system afforded 440 mg of title compound. Elemental analysis: calculated C 63.31; H 10.16; found C 63.17, H 10.11.

EXAMPLE 3

Preparation of 5-fluoro-11,15-bis-triethylsilyloxy-PGI$_2$ methyl ester (formula XIV of Chart B)

The title compound of example 2 (440 mg) was dissolved in 2 ml of tertiary butylbenzene and refluxed for 5 to 90 minutes. TLC showed a new slightly faster running spot which stained rapidly with iodine, behavior characteristic of PGI$_2$. (The methoxyfluoro compound stained very slowly with iodine.) Isolation yielded 365 mg of an oily compound of title compound and compound of formula XVI of Chart B.

EXAMPLE 4

5-fluoro-PGI$_2$ methyl ester (formula XV of Chart B).

Title compound of example 3 (250 mg) was dissolved in dry DMF (3 ml) and stirred with 600 mg of KF for 48 hours. TLC indicated the reaction was essentially complete. Nearly saturated sodium carbonate solution (2 ml) was added and the reaction is extracted with methylene chloride. The methylene chloride layer was washed with water, dried over sodium sulfate and reduced to an oil under nitrogen gas and vacuum. The oil was dissolved in ethyl acetate, diluted with an equal volume of petroleum ether and injected into an low pressure column. Elution with 25% ethyl acetate-petroleum ether solvent system and then 40% ethyl acetate afforded 45 mg of pure amorphous tacky oil of the title product.

EXAMPLE 5

Preparation of 5-fluoro-5-[hexahydro-5-hydroxy-4-(3-hydroxy-1-octenyl)-2H-cyclopenta[b]furan-2-ylidene]pentanoic acid sodium salt. (formula I: X is >C=C(F)— and R$_1$ is ONa)

Title compound of example 4 (45 mg) under nitrogen atmosphere was dissolved in a methanol solution (0.5 ml) of 3.0 mg of sodium hydroxide and 0.05 ml of water. The reaction was allowed to stand at room temperature for 48 hours. Solvent was removed under vacuum and the residue triturated in ethyl acetate until crystalline. The solid was separated by centrification and dried under vacuum to afford the title compound.

EXAMPLE 6

Preparation of 5-fluorohexahydro-5-hydroxy-4-(3-hydroxy-1-octenyl)-2-methoxy-2H-cyclopenta[b]furan-2-pentanoic acid, sodium salt (formula I of Chart A: X is >C(CH$_3$O)—CHF, and R$_1$ is ONa);

When the appropriate starting materials were used in the procedures outlined in Examples 1 through 5 title compound was obtained.

EXAMPLE 7

Preparation of 5-fluorohexahydro-5-hydroxy-4-(3-hydroxy-1-octyenyl)-2-methoxy-2H-cyclopenta[b]furan-2-pentanamide (formula I of Chart A: X is >C(CH$_3$O)—CHF— and R$_1$ is NH$_2$)

Title compound of example 1 was dissolved in methanol (1 ml) and after chilling to −60° C. under nitrogen atmosphere, 1 ml of liquid ammonia was added. A pressure container was sealed and allowed to warm to room temperature. After 14 days the excess ammonia was vented and the reaction is reduced to amorphous solid to afford title compound. Elemental analysis: calculated, C 62.82, H 9.01, N 3.49; found, C, 62.50; H, 8.92; N, 3.28.

EXAMPLE 8

Preparation of 5-fluoro-6-methoxy 11,15-bis-triethylsiloxy-PGI amide

When title compound of example 7 was subjected to the conditions and procedures outlined for the preparation of example 2, title compound was obtained.

EXAMPLE 9

11,15-bis-triethylsiloxy-5-fluoro $PGI_2$ amide (formula XXIV of Chart C: $R_1$ is $NH_2$)

Compound 8 was subjected to pyrolysis conditions described for in example 3 which afforded the title compound.

EXAMPLE 10

Preparation of 5-fluoro $PGI_2$ amide

Title compound example 9 (229 mg) was treated acccording to conditions described in example 4 and 120 mg of the title compound was obtained.

EXAMPLE 11

5-fluoro-6-methoxy-PGI amide (formula I of Chart A: X is $>C(CH_3O)—CHF—$ and $R_1$ is $N(CH_3)_2$)

To a solution of dry benzene (10 ml) under a nitrogen atmosphere was added $(CH_3)_3Al$ in hexane (0.35 ml). The resulting solution was cooled with stirring to around 15° C. and $(CH_3)_2NH$ (0.05 gm) was bubbled into the solution. The reaction was stirred for 20 minutes and then allowed to warm to room temperature. 6-Methoxy-5-fluoro-PGI methyl ester (0.416 gm) in benzene (2 ml) was added rapidly and the reaction then refluxed for 24 hours. The reaction was quenched then warmed and stirred for 1 hour. The organic layer was separated, washed with an appropriate salt solution, and dried over sodium sulfate, and then reduced to an oil under a nitrogen atmosphere and vacuum. The oil was then dissolved in ethyl acetate, injected into a low pressure column, and eluted with ethyl acetate to yield 360 mg of the amide.

EXAMPLE 12

Separation of Isomers of 11,15-bis-triethylsilyloxy-5-fluoro-6-methoxy-$PGI_1$ methyl ester.

The product of example 2 (1.80 g), a mixture of 4 diastereomers, was chromatographed using low pressure liquid chromatography with a 25 mm×1 m column of Woelm Silica Gel which was prewashed with one liter of 95:5 ethylacetatetriethylamine, then with one liter of 96.5:3:0.5 hexane-ethylacetate-triethylamine. The mixture was developed with the same solvent mixture to provide two major fractions. The slower fraction (450 mg) was the 5S,6S isomer, characterized by a $^{13}C$ nmr signal for the 5C at 91.7 ppm coupled to F (J=179$H_2$), and a proton nmr signal for the 6-methoxyl at 3.19 ppm. The faster fraction (1.30 g) was chromatographed on a 25 mm×1 m Florisil column prewashed with 95:5 ethyl acetate-triethylamine, then 98.5:1:0.5 hexane-ethyl acetate-triethylamine. The mixture was developed with this system, producing (after recycling overlap fractions) two fractions. The slower material (160 mg) was the 5S,6R isomer which is characterized by a $^{13}C$ nmr signal at 94.9 ppm with coupling to F (J=177$H_2$) and a proton nmr signal at 3.32 ppm. The faster fraction (1.20 g) was further chromatographed with an high performance liquid chromatography system using a 9.4 mm×500 mm column of Partisil 10 and developed with a 3:97 mixture of ethylacetate and 1,1,2-trichlorotrifluoroethane (recycling overlap fractions) to produce 820 mg of the faster isomer (5R,6S) characterized by a $^{13}C$ nmr signal at 93.1 ppm (J=179 Hz) and a proton nmr signal at 3.28 ppm. The slower isomer (5R,6R) amounted to 265 mg and was characterized by a 13C nmr signal at 92.3 ppm (J=179 Hz) and a proton nmr signal at 3.28 ppm.

EXAMPLE 13

11,15-bis-triethylsilyloxy-5R-fluoro-Δ6-$PGI_1$ methyl ester

1. A mixture of 80 mg of 11,15-bis-triethylsilyloxy-5R-fluoro-6S-methoxy $PGI_1$ methyl ester, 5 mg of magnesium triflate, 2 drops of 2-picoline, and 10 ml of xylene was refluxed for two hours under nitrogen then allowed to cool and filtered. The filtrate was evaporated to a residue which was chromatographed on a 25 g neutral silicic acid column developing with 98:2 hexane-ethyl acetate, then with 95:5 hexane-ethyl acetate to provide 57 mg of the title product and 6 mg of recovered starting material.

2. In a similar manner 165 mg of 11,15-bis-triethylsilyloxy-5R-fluoro-6R-methoxy-$PGI_1$ methyl ester, 5 mg of magnesium triflate, 2 drops of 2-picoline, and 10 ml of xylene was refluxed 18 hours under nitrogen, then worked up as above to yield 106 mg of the title product and 12 mg of the starting material.

EXAMPLE 14

11,15-bis-triethylsilyloxy-5S-fluoro-Δ6-$PGI_1$ methyl ester

1. Using the procedure of example 13, 320 mg of 11,15-bis-triethylsilyloxy-5S-fluoro-6S-methoxy-$PGI_1$ methyl ester was refluxed in 10 ml of xylene with 5 mg of magnesium triflate and 2 drops of 2-picoline for 2 hours. The product was worked up in the same manner to provide 220 mg of product and 25 mg of recovered starting material.

2. In a similar manner 230 mg of 11,15-bis-triethylsilyloxy-5S-fluoro-6R-methoxy-$PGI_1$ methyl ester was refluxed 20 hours to provide 110 mg of the tltle product and 65 mg of recoyered starting material.

EXAMPLE 15

5R-fluoro-Δ6-$PGI_1$ methyl ester

A solution of 57 mg of the product of example 13 in 5 ml of THF was treated with 0.5 ml. of 1M tetrabutylammonium fluoride in THF. After 10 minutes at room temperature, the mixture was diluted with ether, then washed with water and saturated sodium chloride solution. After drying over sodium sulfate and evaporation of solvents, the residue was chromatographed on a 25 g neutral silicic acid column, developing with ethyl acetate to provide 35 mg of the title product.

EXAMPLE 16

5S-fluoro-Δ6-$PGI_1$ methyl ester

Using the procedure of example 15, 264 mg of the product of example 14 was desilylated to provide 133 mg of product.

EXAMPLE 17

5R-fluoro-Δ6-PGI, sodium salt

To a solution of 347 mg of the title product of example 15 in 5 ml of methanol was added 0.95 ml of 1N sodium hydroxide. After 42 hours at room temperature, the mixture was evaporated to a small residue which was dissolved in water filtered and freeze dried to provide 355 mg of the product. The $^{13}C$ nmr spectrum of this compound showed characteristic signals for 5C (89.0 ppm, J=165 Hz), 6C (154.6 ppm, J=21 Hz) and 7C (102.9 ppm, J=6 Hz), with couplings with fluorine.

EXAMPLE 18

5S-fluoro-Δ6-PGI, sodium salt.

Using the procedure of example 17, 264 mg of the product of example 16 was hydrolyzed with 0.72 ml of 1N sodium hydroxide to provide 263 mg of product. The $^{13}C$ nmr spectrum of this compound showed signals for the 5C (89.2 ppm, J=165Hz), 6C (154.3 ppm, J=19 Hz) and 7C (103.8 ppm, J=7 Hz).

CHART A

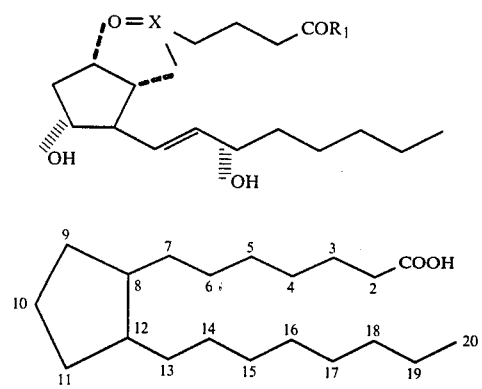

CHART B

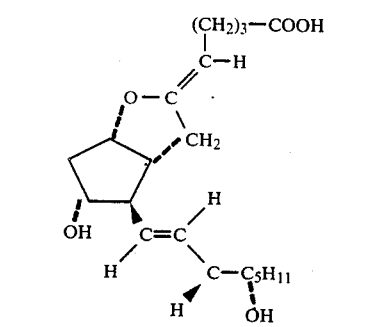

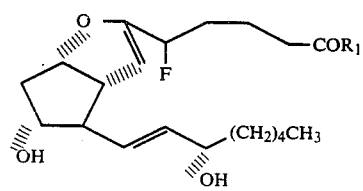

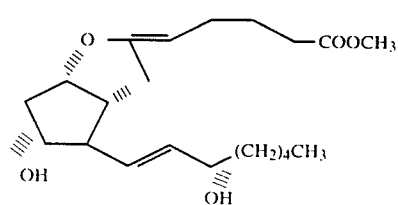

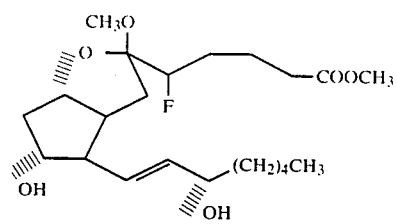

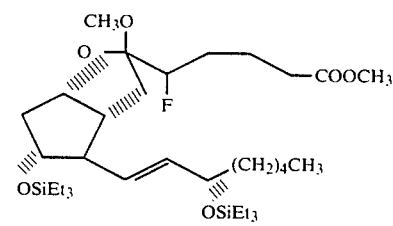

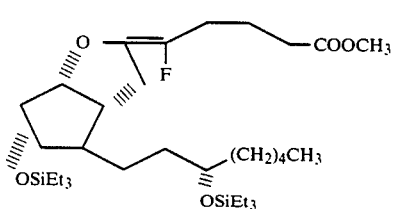

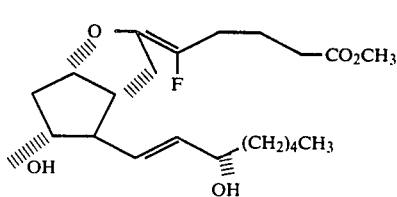

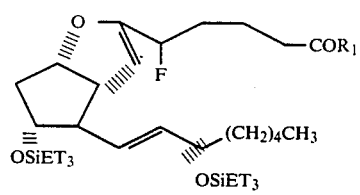

CHART C

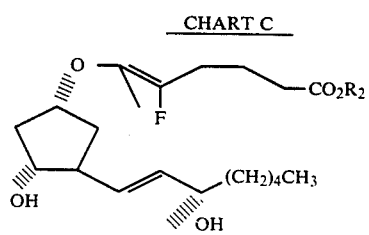

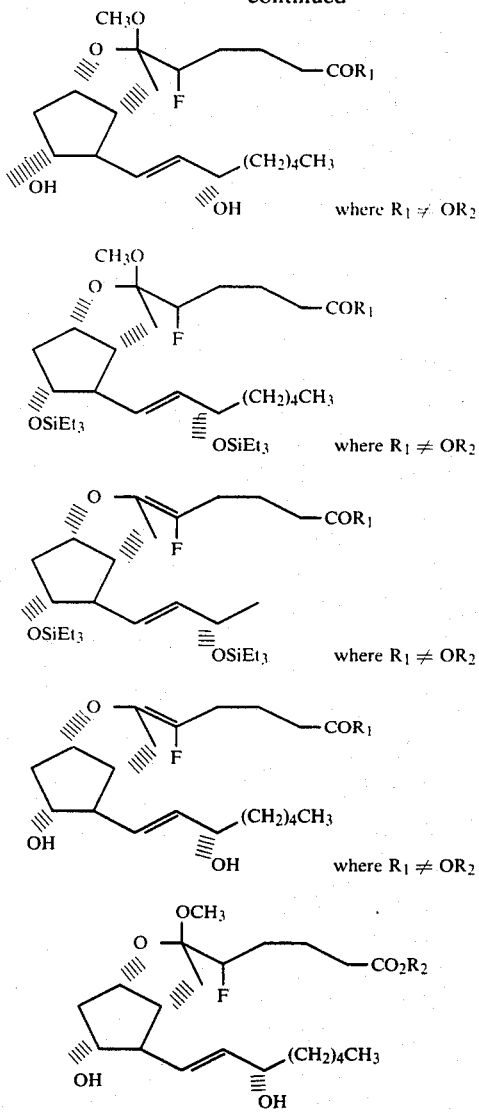

where $R_1 \neq OR_2$ (multiple structures)

What I claim is:
1. A compound of the formula

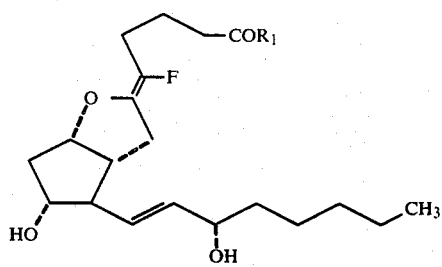

wherein $R_1$ is:
(a) $OR_2$;
(b) $NR_3R_4$;

(c)

XXII 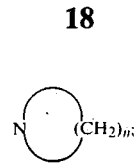

or (d)

XXIII 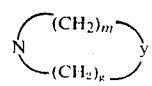

wherein $R_2$ is:
(a) Na+, K+, or ½Ca++
(b) hydroxyalkyl of 1 to 6 C atoms;
(c) hydrogen; or
(d) alkyl of 1 to 6 carbon atoms
wherein $R_3$ is:
(a) hydrogen; or
(b) alkyl of 1 to 6 carbon atoms, inclusive;
wherein $R_4$ is:
(a) hydrogen; or
(b) alkyl of 1 to 6 carbon atoms, inclusive;
wherein n is an integer from 4 to 5; wherein m and q are integers and taken together equal 4 to 5 wherein y is:
(a) O
(b) NH.
2. A compound according to claim 1 of the formula XXVI 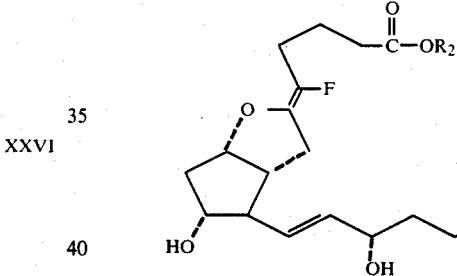

wherein $R_2$ is
(a) Na+, K+, or ½Ca++
(b) hydroxyalkyl of 1 to 6 carbon atoms
(c) hydrogen; or
(d) alkyl of 1 to 6 carbon atoms.
3. A compound, according to claim 1, of the formula

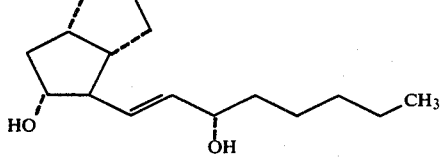

* * * * *

UNITED STATES PATENT AND TRADEMARK OFFICE
CERTIFICATE OF CORRECTION

PATENT NO. : 4,670,569

DATED : June 2, 1987

INVENTOR(S) : Nysted, et al.

It is certified that error appears in the above-identified patent and that said Letters Patent are hereby corrected as shown below:

Column 15, Chart A, the third structure, that portion of the structure reading

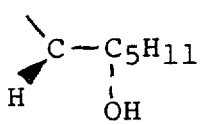  should read  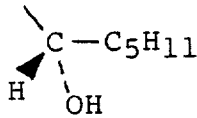

Column 16, the last structure, Chart C, that portion of the structure reading

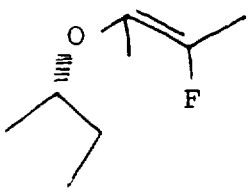  should read  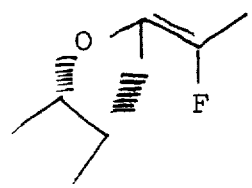

Claim 1, the second ring system in column 18 relating to substituents of $R_1$ [section (d)], that portion of the ring system reading

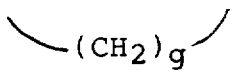  should read  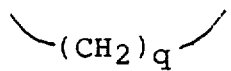

UNITED STATES PATENT AND TRADEMARK OFFICE
CERTIFICATE OF CORRECTION

PATENT NO. : 4,670,569
DATED : June 2, 1987
INVENTOR(S) : Nysted, et al.

It is certified that error appears in the above-identified patent and that said Letters Patent are hereby corrected as shown below:

Column 16, the first structure (Chart B, XI), that portion of the structure reading

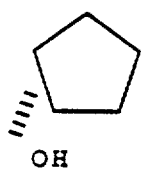   should read   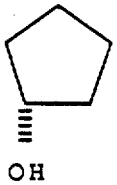

Column 16, the first structure (Chart B, XI), that portion of the structure reading

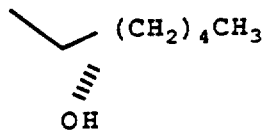   should read   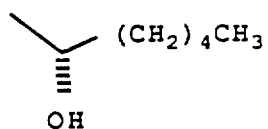

Column 16, the third structure (Chart B, XIII), that portion of the structure reading

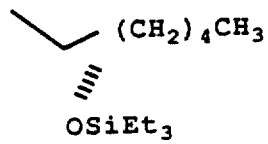   should read   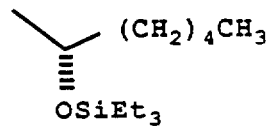

UNITED STATES PATENT AND TRADEMARK OFFICE
CERTIFICATE OF CORRECTION

PATENT NO. : 4,670,569

DATED : June 2, 1987

INVENTOR(S) : Nysted, et al.

It is certified that error appears in the above-identified patent and that said Letters Patent are hereby corrected as shown below:

Column 16, the fourth structure (Chart B, XIV), that portion of the structure reading

     should read     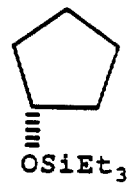

UNITED STATES PATENT AND TRADEMARK OFFICE
CERTIFICATE OF CORRECTION

PATENT NO. : 4,670,569
DATED : June 2, 1987
INVENTOR(S) : Nysted, et al

It is certified that error appears in the above-identified patent and that said Letters Patent is hereby corrected as shown below:

Column 16, the fifth structure (Chart B, XV), that portion of the structure reading

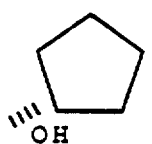 should read 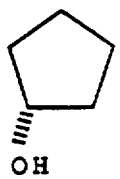

Signed and Sealed this

Twentieth Day of December, 1988

Attest:

DONALD J. QUIGG

Attesting Officer

Commissioner of Patents and Trademarks